(12) United States Patent
Dreyfuss

(10) Patent No.: US 8,202,306 B2
(45) Date of Patent: Jun. 19, 2012

(54) MESH REINFORCED TISSUE ANCHOR

(75) Inventor: Peter J. Dreyfuss, Naples, FL (US)

(73) Assignee: Arthrex, Inc., Naples, FL (US)

( * ) Notice: Subject to any disclaimer, the term of this patent is extended or adjusted under 35 U.S.C. 154(b) by 793 days.

(21) Appl. No.: 11/518,908

(22) Filed: Sep. 12, 2006

(65) Prior Publication Data

US 2007/0060923 A1 Mar. 15, 2007

Related U.S. Application Data

(60) Provisional application No. 60/715,616, filed on Sep. 12, 2005.

(51) Int. Cl.
| | |
|---|---|
| *A61B 17/04* | (2006.01) |
| *A61B 17/84* | (2006.01) |
| *A61B 17/86* | (2006.01) |
| *A61B 17/08* | (2006.01) |
| *A61F 2/08* | (2006.01) |
| *A61D 1/00* | (2006.01) |

(52) U.S. Cl. ........................ 606/329; 606/213
(58) Field of Classification Search .............. 606/300, 606/329, 213–218, 219, 228–232, 304, 305, 606/308; 411/455, 480, 482, 486
See application file for complete search history.

(56) References Cited

U.S. PATENT DOCUMENTS

| | | | | | |
|---|---|---|---|---|---|
| 4,064,567 | A | * | 12/1977 | Burstein et al. | 623/23.46 |
| 5,456,721 | A | * | 10/1995 | Legrand | 623/13.15 |
| 5,578,086 | A | * | 11/1996 | Prescott | 623/11.11 |
| 5,964,783 | A | * | 10/1999 | Grafton et al. | 606/232 |
| 6,517,564 | B1 | * | 2/2003 | Grafton et al. | 606/213 |
| 6,520,964 | B2 | * | 2/2003 | Tallarida et al. | 606/71 |
| 6,623,492 | B1 | * | 9/2003 | Berube et al. | 606/151 |
| 7,488,347 | B1 | * | 2/2009 | Goble et al. | 623/18.11 |
| 2003/0032961 | A1 | * | 2/2003 | Pelo et al. | 606/72 |
| 2004/0087981 | A1 | * | 5/2004 | Berube et al. | 606/151 |
| 2005/0125077 | A1 | * | 6/2005 | Harmon et al. | 623/23.72 |
| 2005/0246021 | A1 | * | 11/2005 | Ringeisen et al. | 623/17.11 |
| 2006/0036251 | A1 | * | 2/2006 | Reiley | 606/72 |

FOREIGN PATENT DOCUMENTS

| | | |
|---|---|---|
| EP | 1 264 607 A1 | 12/2002 |
| WO | WO 01/54592 A1 | 8/2001 |
| WO | WO 2004/069100 A2 | 8/2004 |

* cited by examiner

*Primary Examiner* — Kevin T Truong
*Assistant Examiner* — David Bates
(74) *Attorney, Agent, or Firm* — Dickstein Shapiro LLP

(57) ABSTRACT

A tissue anchor or tack that is reinforced by a three-dimensional mesh for improved strength and structural support for the tissue tack. The three-dimensional mesh may be formed of a bioabsorbable or non-absorbable material and may comprise fibers which are weaved, laced, crosslinked, or glued together, for example. The three-dimensional mesh may be also provided by molding a suitable pre-polymeric compound into a shape which directly provides the desired mesh structure. The three-dimensional mesh is preferably molded into the tissue tack. The mesh reinforced tissue tack is preferably cannulated and has a tack shaped configuration.

4 Claims, 6 Drawing Sheets

MESH REINFORCED TISSUE ANCHOR

CROSS-REFERENCE TO RELATED APPLICATIONS

This application claims the benefit of U.S. Provisional Application Ser. No. 60/715,616, filed Sep. 12, 2005, the entire disclosure of which is incorporated by reference herein.

FIELD OF THE INVENTION

The present invention is directed to sutureless fixation of tissue to bone and, more specifically, to a mesh reinforced tissue anchor with an angled or straight head for sutureless tissue fixation.

BACKGROUND OF THE INVENTION

When soft tissue tears away from bone, reattachment becomes necessary. Various fixation devices, including sutures, screws, staples, wedges, and plugs have been used in the past to secure soft tissue to bone. More recently, various types of threaded suture anchors have been developed.

The known suture anchors generally require that the surgeon tie knots in the suture to secure tissue to the bone. Tying surgical knots is tedious and time consuming. It would be preferable to be able to secure the soft tissue to the bone in one step without having to tie knots.

Accordingly, a need exists for a bioabsorbable anchor for soft tissue fixation that can be installed to secure tissue easily and effectively without sutures, and yet can provide improved anchoring capabilities. A need also exists for a soft tissue fixation device having a low profile configuration and improved structural properties.

SUMMARY OF THE INVENTION

The present invention overcomes disadvantages of the prior art and fulfills the needs discussed above by providing a tissue anchor or tack that is reinforced by a three-dimensional mesh for improved strength and structural support for the tissue tack. The three-dimensional mesh may be formed of a bioabsorbable or non-absorbable material and may comprise fibers which are weaved, laced, crosslinked, or glued together, for example. The three-dimensional mesh may be also provided by molding a suitable pre-polymeric compound into a shape which directly provides the desired mesh structure. The three-dimensional mesh is preferably molded into the tissue tack.

The mesh reinforced tissue tack is preferably cannulated and has a tack shaped configuration. The head of the tack may be oblong to provide a low-profile, and is mounted on a cannulated shaft. The head may be mounted at a perpendicular angle to the shaft or, alternatively, at an anatomic angle.

The mesh reinforced tissue anchor of the present invention may be employed for sutureless fixation of soft tissue to bone, providing improved anchoring and structural capabilities. A method for sutureless fixation of soft tissue to bone according to the present invention comprises the steps of: (i) providing a tissue anchor that is reinforced by a three-dimensional mesh which may be formed of a bioabsorbable or non-absorbable material and which may comprise fibers which are weaved, laced, crosslinked, or glued together, for example; and (ii) attaching the soft tissue to bone using the mesh reinforced suture anchor.

These and other features and advantages of the invention will be more apparent from the following detailed description that is provided in connection with the accompanying drawings and illustrated exemplary embodiments of the invention.

DETAILED DESCRIPTION OF THE PREFERRED EMBODIMENT

The following description is provided to enable any person skilled in the art to make and use the invention and sets forth the best modes contemplated by the inventors of carrying out their invention. Various modifications, however, will remain readily apparent to those skilled in the art.

Figure 1:
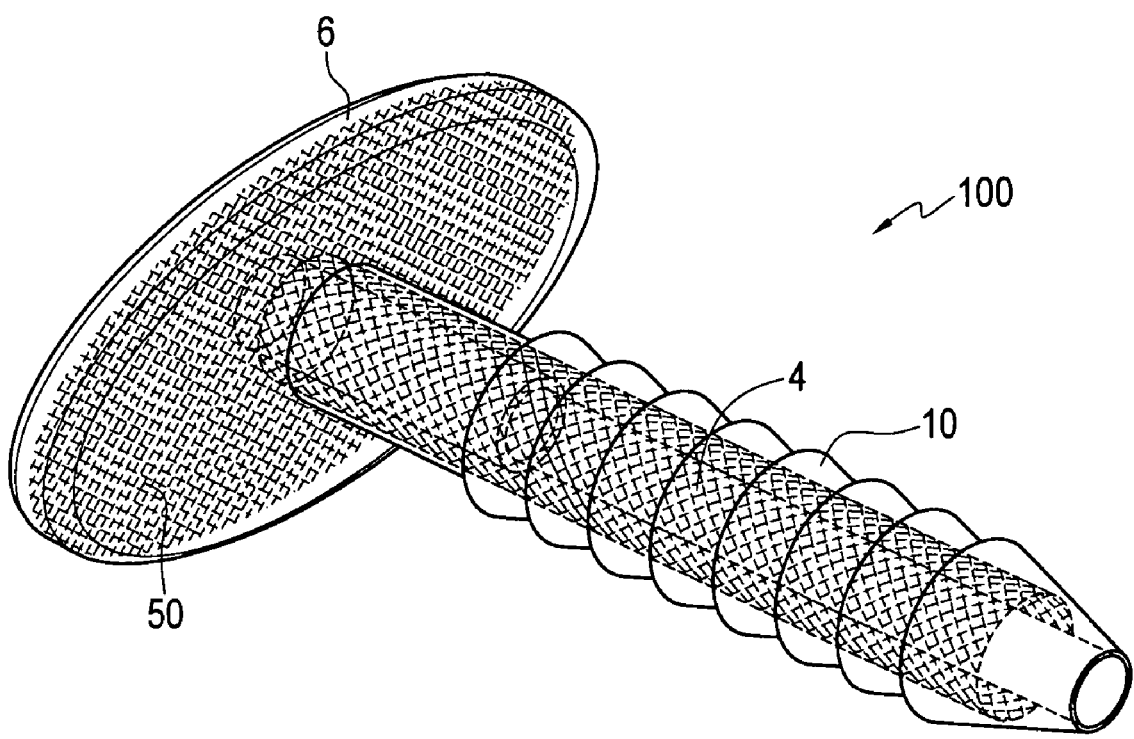
FIG. 1 is a perspective view of a mesh reinforced tissue anchor of the present invention.
Figure 2:
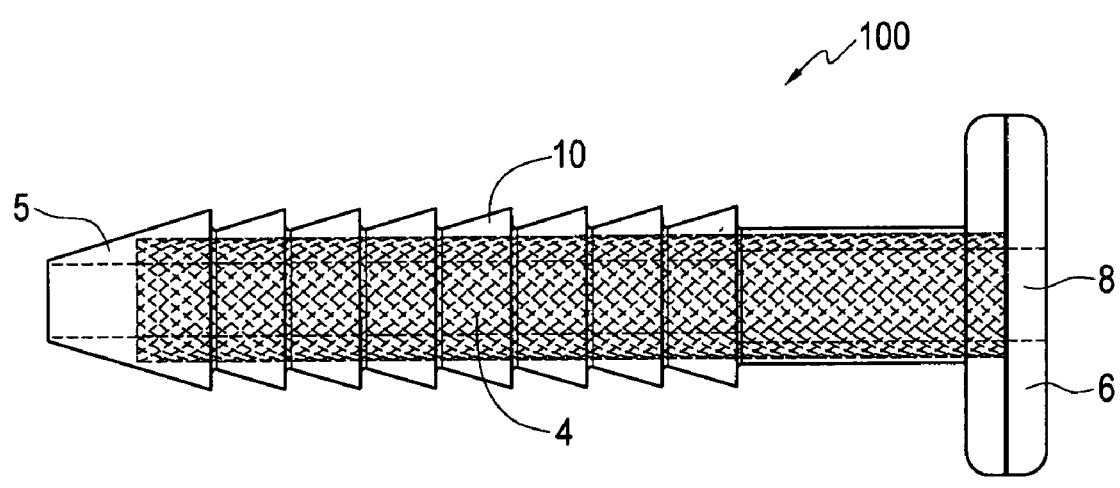
FIG. 2 is a side view of the mesh reinforced tissue anchor of FIG. 1.
Figure 3:
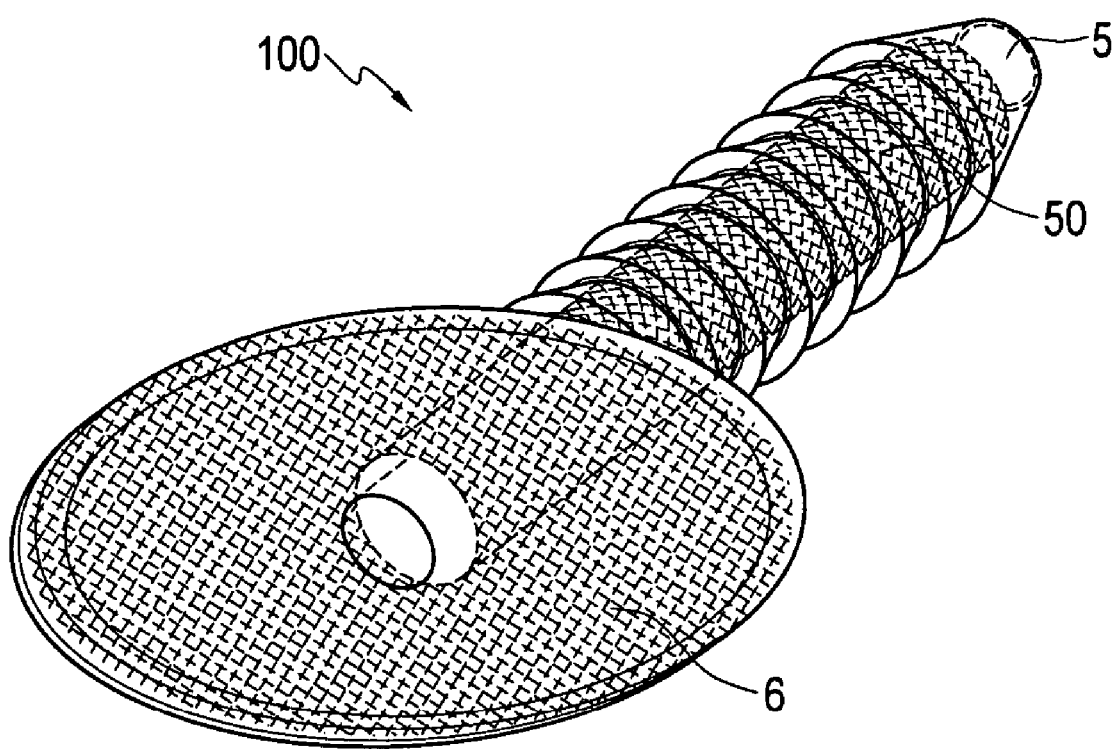
FIG. 3 is another perspective view of the mesh reinforced tissue anchor of FIG. 1.
Figure 4:
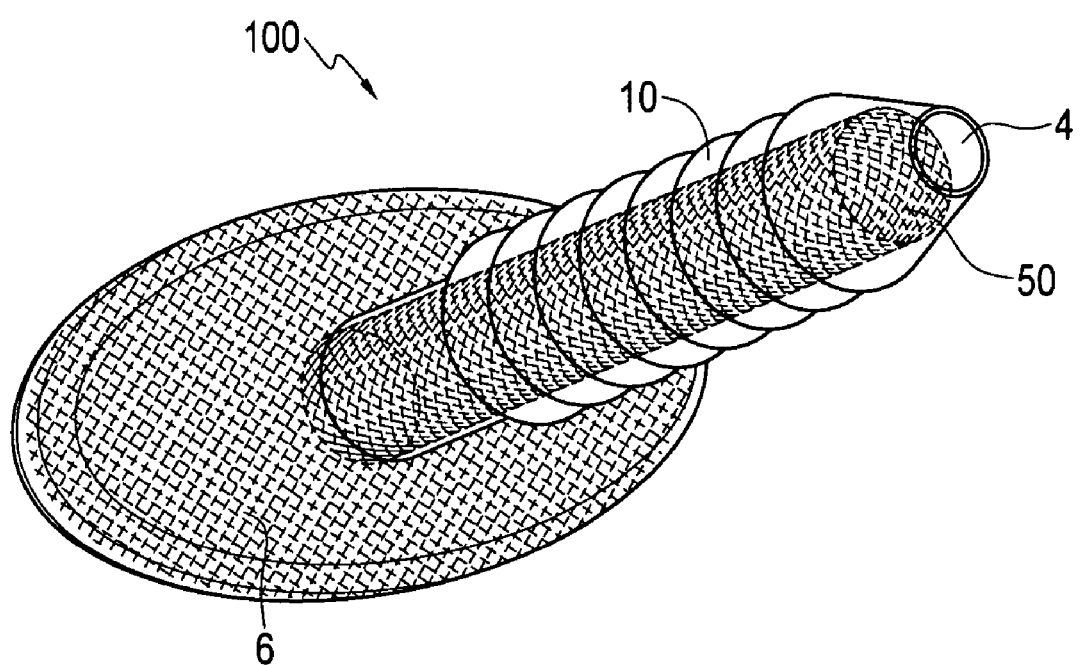
FIG. 4 is another perspective view of the mesh reinforced tissue anchor of FIG. 1.
Figure 5:
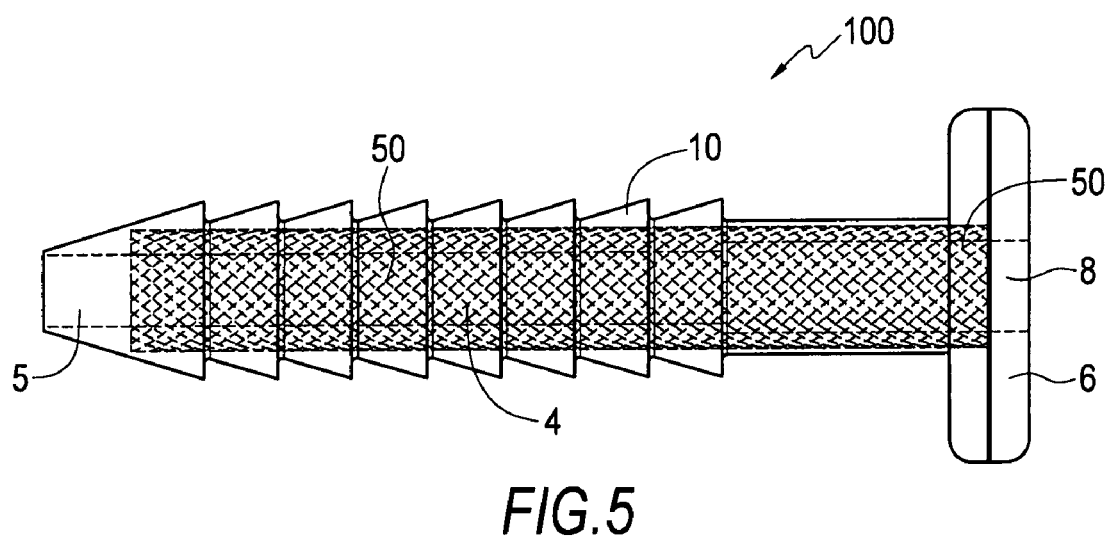
FIG. 5 is another cross-sectional view of the mesh reinforced tissue anchor of FIG. 1.
Figure 6:
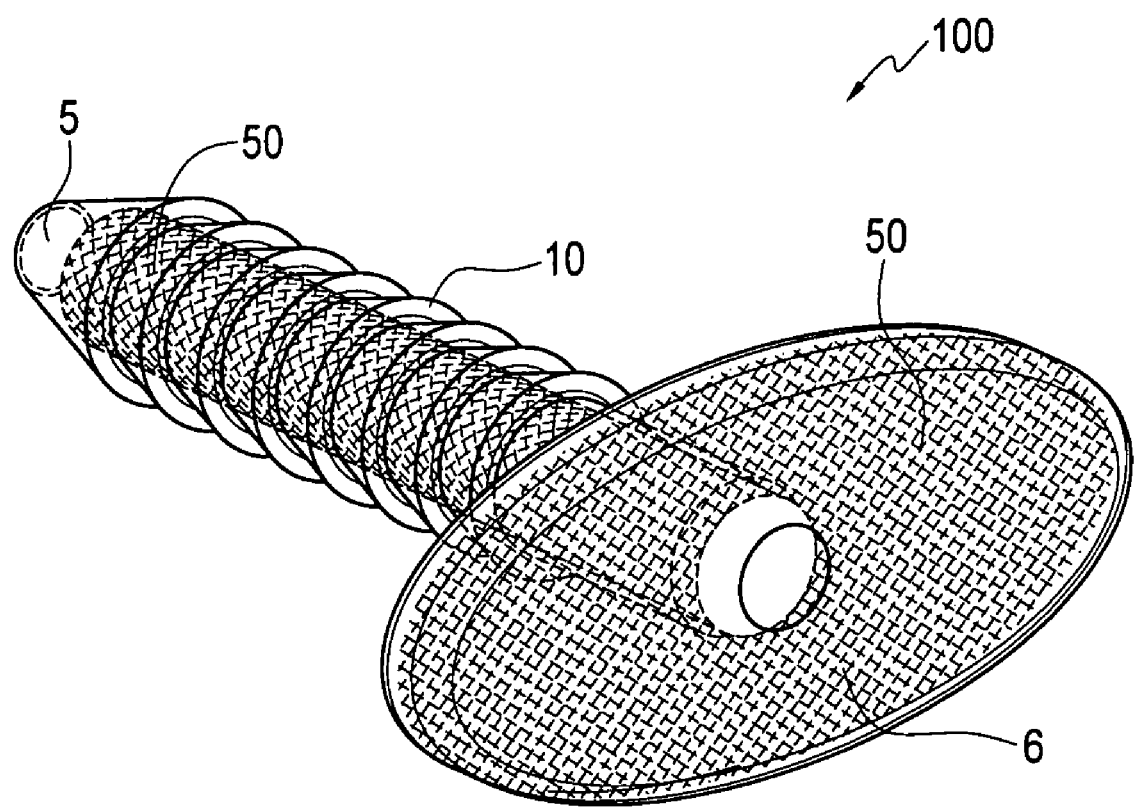
FIG. 6 is another perspective view of the mesh reinforced tissue anchor of FIG. 1.

FIGS. 1-6 illustrate a tissue anchor or tack 100 reinforced with a three-dimensional mesh 50 according to the present invention. Tissue anchor 100 may be formed of bioabsorbable or non-absorbable material. Tissue anchor 100 includes a cannulated shaft 4 with an oval-shaped cannulated head 6 disposed on the proximal end of the shaft. Tissue anchor 100 has a blunt (i.e., flat) tip 5. In the embodiment of the invention shown in FIGS. 1-6, the head 6 is formed at a perpendicular angle with respect to the shaft 4. A cannula 8 extends continuously through the entire length of the anchor 100, i.e., through both the head 6 and the tip 5 as well as the shaft 4.

Anchor 100 is provided with ribs 10 formed circumferentially at least partially around and partially along the length of shaft 4. Ribs 10 have a truncated, conical shape, increasing in diameter toward the head of the tack at an angle of preferably 15° with respect to the longitudinal axis of tack 100, and reaching a major diameter of 3.0 mm. Slots 12 (not shown) may be formed in ribs 10 on alternating sides of shaft 4. The slots provide access for ingrowth of bony tissue for enhanced pullout strength.

Although FIGS. 1-6 illustrate an embodiment according to which the oval-shaped cannulated head 6 is perpendicular to the longitudinal axis of the tack, the invention also contemplates embodiments wherein the tissue tack is provided with an angled head. Details of these particular embodiments are presented in U.S. Pat. No. 6,517,564, issued on Feb. 11, 2003, the disclosure of which is incorporated by reference in its entirety.

The preferred material for the anchor is a non-crystalline, amorphous poly (L-lactide-co-D,L-lactide) 70%:30% (PLDLA) copolymer. This material reduces tissue reaction. The anchor becomes encapsulated by fibrous tissue within six weeks after implantation, and generally degrades within 12 to 16 months. Although PLDLA is the most preferred material, other bioabsorbable or non-absorbable materials known in the art can be utilized. As used herein, "bioabsorbable" is considered to be interchangeable with biodegradable, resorbable and absorbable to mean that the device can be absorbed by the body over time.

As used in the present application, the term "mesh" is defined as a set of pre-existing fibers, cords, threads, or material that define a set of open spaces and that can be formed into a stable, three-dimensional matrix or network by cross-linking, gluing, weaving, lacing, or other similar methods. For example, the mesh may comprise single or multiple strands of fibers that are interlaced or woven into a desired three-dimensional mesh-type structure. Alternatively, the mesh may be formed by cross-linking, gluing or similar treatment of single or multiple strands of fibers. The mesh of the present invention may be also formed by molding a pre-polymeric compound (for example, a monomeric compound) or a polymeric compound into a shape that directly provides the desired three-dimensional mesh-type structure. In this embodiment, monomers may be reacted while suspended in a solvent which is subsequently removed by lyophilization. In yet another embodiment, a liquid polymer or pre-polymer may be poured into a mold that establishes the three-dimensional mesh.

In a preferred embodiment, mesh 50 is insert molded into at least a portion of the head 6 and at least a portion of the shaft 4 and, preferably, into the whole head 6 and shaft 4. As noted above, mesh 50 is preferably three-dimensional and comprises fibers which are weaved, laced, crosslinked, or glued together, for example. In an alternative embodiment, the three-dimensional mesh may be provided by molding a suitable pre-polymeric compound into a shape which directly provides the desired mesh structure. The three-dimensional mesh may be formed of a bioabsorbable or non-absorbable material.

In an alternative embodiment, mesh 50 may comprise collagen fibers that provide a growth matrix for tissue once the bioabsorbable material of the tissue anchor degrades. If desired, the mesh 50 may optionally comprise a growth factor and/or an antiseptic. The term "growth factor" as used in the present application is intended to include all factors, such as proteinaceous factors, for example, which play a role in the induction or conduction of growth of bone, ligaments, cartilage or other tissues associated with bone or joints. In particular, these growth factors include bFGF, aFGF, EGF (epidermal growth factor), PDGF (platelet-derived growth factor), IGF (insulin-like growth factor), TGF-$\beta$. I through III, including the TGF-$\beta$. superfamily (BMP-1 through 12, GDF 1 through 12, dpp, 60A, BIP, OF).

The mesh reinforced tissue anchor of the present invention provides sutureless fixation of soft tissue to bone and improved anchoring and structural capabilities. A method for sutureless fixation of soft tissue to bone according to the present invention comprises the steps of: (i) providing a tissue anchor that is reinforced by a three-dimensional mesh which may be formed of a bioabsorbable or non-absorbable material and which may comprise fibers which are weaved, laced, crosslinked, or glued together, for example; and (ii) attaching the soft tissue to bone using the mesh reinforced suture anchor.

Preferred indications for the improved tissue anchor or tack of the present invention include arthroscopic or open repair of glenohumeral joint pathologies. These include reattachment of the glenoid labrum or inferior glenohumeral ligament in patients with primary or recurrent anterior dislocation or subluxation of the shoulder, in association with adequate postoperative immobilization. Indications for the improved tissue anchor or tack of the present invention also include rotator cuff repairs, SLAP lesions repairs and instability repairs, among others. The mesh reinforced suture anchor of the present invention may be employed, for example, in arthroscopic procedures such as a Bankart repair detailed in U.S. Pat. No. 6,517,564, issued on Feb. 11, 2003, the disclosure of which is incorporated by reference in its entirety.

The above description and drawings illustrate preferred embodiments which achieve the objects, features and advantages of the present invention. It is not intended that the present invention be limited to the illustrated embodiments. Any modification of the present invention which comes within the spirit and scope of the following claims should be considered part of the present invention.

What is claimed as new and desired to be protected by Letters Patent of the United States is:

1. A bioabsorbable tissue tack for sutureless fixation of soft tissue to bone, comprising:
    a shaft having a proximal end and a distal end, the shaft being fully cannulated from the proximal end to the distal end for insertion of the tissue tack over a guide wire;
    a plurality of ribs formed circumferentially on the cannulated shaft, the plurality of ribs having a truncated, conical shape;
    a cannulated, longitudinally oblong head as viewed along a central axis of the shaft disposed on the proximal end of the shaft for anchoring soft tissue to bone without sutures; and
    a separate bioabsorable collagen three-dimensional mesh insert molded in the cannulated shaft and the whole longitudinally oblong head, to reinforce the tissue tack.

2. The tissue tack of claim 1, wherein the three-dimensional mesh comprises a growth factor.

3. The tissue tack of claim 1, wherein the three-dimensional mesh comprises an antiseptic.

4. The tissue tack of claim 1, wherein the oblong head is disposed at a non-perpendicular angle to the central axis of the cannulated shaft.

\* \* \* \* \*